(12) United States Patent
Finlay

(10) Patent No.: US 9,144,621 B1
(45) Date of Patent: Sep. 29, 2015

(54) AIR FRESHENER CANISTER WITH PULL TOP

(71) Applicant: American Covers, Inc., Draper, UT (US)

(72) Inventor: Nathanael Finlay, Lehi, UT (US)

(73) Assignee: American Covers, Inc., Draper, UT (US)

( * ) Notice: Subject to any disclaimer, the term of this patent is extended or adjusted under 35 U.S.C. 154(b) by 369 days.

(21) Appl. No.: 13/722,782

(22) Filed: Dec. 20, 2012

Related U.S. Application Data

(60) Provisional application No. 61/584,917, filed on Jan. 10, 2012.

(51) Int. Cl.
*A61L 9/12* (2006.01)

(52) U.S. Cl.
CPC .............. *A61L 9/12* (2013.01); *A61L 2209/13* (2013.01)

(58) Field of Classification Search
CPC ............ A61L 2209/13; A61L 2209/15; A61L 2209/11; A61L 9/12
USPC ...................................................... 239/53–60
See application file for complete search history.

(56) References Cited

U.S. PATENT DOCUMENTS

| | | |
|---|---|---|
| D176,671 S | 4/1876 | Myers |
| 369,878 A | 9/1887 | Palmer |
| 1,171,737 A | 2/1916 | Madgan |
| 2,244,944 A | 6/1941 | Furlonge |
| D140,109 S | 1/1945 | Pierce |
| 2,642,248 A | 6/1953 | Semon |
| 2,733,333 A | 1/1956 | Peters |
| D177,826 S | 5/1956 | Katz |
| D178,237 S | 7/1956 | Katz |
| 3,239,145 A | 3/1966 | Aurelio |
| 3,456,106 A | 7/1969 | Glchkin |
| 3,655,129 A | 4/1972 | Seiner |
| 3,847,305 A | 11/1974 | Tobin |
| 3,948,445 A | 4/1976 | Andeweg |
| 3,971,858 A | 7/1976 | Collier et al. |
| D246,986 S | 1/1978 | Costello |
| 4,084,079 A | 4/1978 | Costello |

(Continued)

FOREIGN PATENT DOCUMENTS

| | | |
|---|---|---|
| CA | 2077251 | 5/1993 |
| EP | 0 348 970 | 1/1990 |

(Continued)

OTHER PUBLICATIONS

U.S. Appl. No. 12/979,763, filed Dec. 28, 2010, Aaron Irvin notice of allowance dated Apr. 15, 2013.

(Continued)

*Primary Examiner* — Jason Boeckmann
(74) *Attorney, Agent, or Firm* — Thorpe North & Western LLP

(57) ABSTRACT

An air freshener includes a canister having an open top and a fragrant material including a desired fragrance carried by a carrier and disposed in the canister. A grid is disposed in and fixedly secured to the canister and over the fragrant material. A pull top is releasably secured to the canister and extends over the open top to form a sealed container containing the fragrant material and the grid. The pull top is selectively removable from the canister to expose the grid therein, and allow release of the desired fragrance through the grid.

18 Claims, 10 Drawing Sheets

(56) References Cited

U.S. PATENT DOCUMENTS

| | | |
|---|---|---|
| D250,041 S | 10/1978 | Schimanski |
| 4,149,675 A | 4/1979 | Van Breen et al. |
| 4,173,604 A * | 11/1979 | Dimacopoulos ............... 261/30 |
| 4,184,099 A | 1/1980 | Lindauer et al. |
| 4,226,944 A | 10/1980 | Stone et al. |
| D258,511 S | 3/1981 | Ashton |
| 4,280,649 A | 7/1981 | Montealegre |
| 4,301,949 A | 11/1981 | Palson et al. |
| 1,683,545 A | 9/1982 | Harris |
| 4,382,548 A | 5/1983 | van der Heijden |
| 4,391,781 A | 7/1983 | van Lit |
| 4,517,326 A | 5/1985 | Cordts et al. |
| 4,549,693 A | 10/1985 | Barlics |
| 4,594,380 A | 6/1986 | Chapin et al. |
| D286,323 S | 10/1986 | Haworth |
| 4,638,057 A | 1/1987 | Takahashi et al. |
| 4,649,046 A | 3/1987 | Kross |
| 4,703,070 A | 10/1987 | Locko et al. |
| RE32,834 E | 1/1989 | Cordts et al. |
| 4,808,347 A | 2/1989 | Dawn |
| 4,840,773 A | 6/1989 | Wade |
| 4,849,606 A | 7/1989 | Martens et al. |
| 4,874,129 A | 10/1989 | DiSapio et al. |
| 4,880,690 A | 11/1989 | Szycher et al. |
| 4,950,542 A | 8/1990 | Barker |
| 4,967,988 A | 11/1990 | Nguyen |
| 4,968,456 A | 11/1990 | Muderlak et al. |
| 5,008,115 A | 4/1991 | Lee et al. |
| 5,019,434 A | 5/1991 | Matsumoto |
| 5,034,222 A | 7/1991 | Kellett et al. |
| D319,781 S | 9/1991 | Halm et al. |
| 5,050,798 A | 9/1991 | Sullivan |
| D322,558 S | 12/1991 | Halm et al. |
| 5,071,704 A | 12/1991 | Fischel-Ghodsian |
| 5,114,625 A | 5/1992 | Gibson |
| 5,120,583 A | 6/1992 | Garcia |
| 5,178,327 A | 1/1993 | Palamand et al. |
| 5,180,107 A | 1/1993 | Lindauer |
| 5,193,445 A | 3/1993 | Ferguson |
| D334,975 S | 4/1993 | Bunce |
| 5,208,027 A | 5/1993 | Weder et al. |
| 5,220,636 A | 6/1993 | Chang |
| D338,519 S | 8/1993 | Peterson |
| 5,234,162 A | 8/1993 | Sullivan |
| 5,240,487 A | 8/1993 | Kung |
| D349,157 S | 7/1994 | Rymer |
| D350,192 S | 8/1994 | Patel et al. |
| 5,368,822 A | 11/1994 | McNeil |
| 5,407,642 A | 4/1995 | Lord |
| 5,422,078 A | 6/1995 | Colon |
| D367,526 S | 2/1996 | Bignon |
| D367,924 S | 3/1996 | Patel et al. |
| 5,520,921 A | 5/1996 | Chalifoux |
| D373,626 S | 9/1996 | Dente et al. |
| D375,350 S | 11/1996 | Patel et al. |
| 5,595,194 A | 1/1997 | Talbot |
| D380,258 S | 6/1997 | Muller et al. |
| 5,651,522 A | 7/1997 | Davis et al. |
| 5,683,285 A | 11/1997 | Wong |
| 5,695,692 A | 12/1997 | Kennedy |
| 5,704,832 A | 1/1998 | Borrell |
| D390,941 S | 2/1998 | Cessaroni et al. |
| D392,032 S | 3/1998 | Zaragoza et al. |
| 5,762,549 A | 6/1998 | Scheuer et al. |
| 5,780,527 A | 7/1998 | O'Leary |
| 2,794,767 A | 8/1998 | Wilson |
| 5,820,791 A | 10/1998 | Canale |
| D400,662 S | 11/1998 | Davis |
| 5,845,847 A | 12/1998 | Martin et al. |
| 5,860,552 A | 1/1999 | Culhane et al. |
| 5,861,128 A | 1/1999 | Vick et al. |
| D404,957 S | 2/1999 | Cheris et al. |
| 5,871,765 A | 2/1999 | Johnson et al. |
| 5,899,382 A | 5/1999 | Hayes |
| D410,540 S | 6/1999 | Pinchuk |
| D411,002 S | 6/1999 | Farmer |
| D415,267 S | 10/1999 | Kauzlarich et al. |
| D415,268 S | 10/1999 | Farmer |
| 5,988,520 A | 11/1999 | Bitner |
| D417,727 S | 12/1999 | Christianson |
| 6,044,202 A | 3/2000 | Junkel |
| D424,677 S | 5/2000 | Chen |
| D425,190 S | 5/2000 | Morikawa |
| 6,102,660 A | 8/2000 | Lee |
| 6,111,055 A | 8/2000 | Berger et al. |
| 6,123,906 A | 9/2000 | Farmer |
| 6,123,935 A | 9/2000 | Wefler et al. |
| D432,222 S | 10/2000 | Rymer et al. |
| D435,694 S | 12/2000 | Lebherz |
| D437,038 S | 1/2001 | Chuan |
| 6,190,607 B1 | 2/2001 | Farmer |
| 6,191,197 B1 | 2/2001 | Wang et al. |
| 6,197,263 B1 | 3/2001 | Blount |
| 6,202,938 B1 | 3/2001 | Collier |
| D440,294 S | 4/2001 | Bilek |
| D441,441 S | 5/2001 | Upson |
| 6,264,887 B1 | 7/2001 | Farmer |
| 6,291,371 B1 | 9/2001 | Shefer et al. |
| 6,309,715 B1 | 10/2001 | Lindauer et al. |
| 6,325,475 B1 | 12/2001 | Hayes et al. |
| D454,190 S | 3/2002 | Trocola |
| 6,357,260 B1 | 3/2002 | Lutz |
| 6,374,044 B1 | 4/2002 | Freidel |
| 6,375,966 B1 | 4/2002 | Maleeny et al. |
| 6,379,689 B1 | 4/2002 | Aguadisch |
| 6,416,043 B1 | 7/2002 | Eisenbraun |
| 6,514,467 B1 | 2/2003 | Bulsink et al. |
| D472,968 S | 4/2003 | Christianson |
| D478,379 S | 8/2003 | Talenton et al. |
| D478,973 S | 8/2003 | Wagner |
| D479,592 S | 9/2003 | Lammel et al. |
| D485,343 S | 1/2004 | Wu |
| D487,504 S | 3/2004 | Yuen |
| 6,712,286 B2 | 3/2004 | Baxter et al. |
| D488,214 S | 4/2004 | Quantin |
| D488,548 S | 4/2004 | Lablaine |
| D491,257 S | 6/2004 | Picken |
| D491,798 S | 6/2004 | Buthier |
| D496,720 S | 9/2004 | Dudley |
| 6,800,252 B1 | 10/2004 | Jedzinski |
| 6,885,811 B2 | 4/2005 | He et al. |
| D504,943 S | 5/2005 | Dudley |
| D507,341 S | 7/2005 | Taylor |
| D511,568 S | 11/2005 | Wheatley |
| D514,679 S | 2/2006 | Wheatley |
| D515,192 S | 2/2006 | Smith et al. |
| 7,025,283 B2 | 4/2006 | Torres |
| 7,055,764 B1 | 6/2006 | Martinez et al. |
| 7,061,386 B2 | 6/2006 | Seresini |
| 7,070,172 B2 | 7/2006 | Fabrega et al. |
| 7,137,570 B2 | 11/2006 | Wheatley et al. |
| D535,376 S | 1/2007 | Michaels et al. |
| D535,379 S | 1/2007 | Hundertmark |
| 7,159,792 B2 | 1/2007 | Wheatley et al. |
| D544,080 S | 6/2007 | Carlson |
| D544,084 S | 6/2007 | Michaels et al. |
| D544,594 S | 6/2007 | Zobele |
| D544,953 S | 6/2007 | Kee |
| D546,432 S | 7/2007 | Hundertmark |
| 7,243,859 B2 | 7/2007 | Caserta et al. |
| D548,317 S | 8/2007 | Newton et al. |
| D550,345 S | 9/2007 | Weggelaar |
| D551,333 S | 9/2007 | Wu |
| D554,746 S | 11/2007 | Davis et al. |
| 7,293,719 B2 | 11/2007 | Wheatley |
| D565,162 S | 3/2008 | Carlson |
| 7,344,123 B2 | 3/2008 | Pankhurst et al. |
| D565,715 S | 4/2008 | Wu |
| D573,706 S | 7/2008 | Zlotnik et al. |
| D574,941 S | 8/2008 | Weggelaar |
| 7,441,360 B2 | 10/2008 | Christianson et al. |
| D580,039 S | 11/2008 | Zlotnik et al. |
| D585,129 S | 1/2009 | Huang |
| D585,971 S | 2/2009 | Carrizales |

(56) References Cited

U.S. PATENT DOCUMENTS

| | | |
|---|---|---|
| D591,415 S | 4/2009 | Wu |
| D593,670 S | 6/2009 | Valentino et al. |
| D594,953 S | 6/2009 | King et al. |
| D594,954 S | 6/2009 | Wheatley |
| 7,544,332 B2 | 6/2009 | De Silva et al. |
| D597,645 S | 8/2009 | Thompson |
| D598,531 S | 8/2009 | Irvin |
| D607,983 S | 1/2010 | Irvin |
| 7,651,666 B2 | 1/2010 | Adair et al. |
| 7,670,566 B2 | 3/2010 | Adair et al. |
| 7,687,037 B2 | 3/2010 | Wheatley |
| 7,687,038 B2 | 3/2010 | Wheatley |
| D614,277 S | 4/2010 | Hsiao |
| D619,692 S | 7/2010 | Hami et al. |
| D619,693 S | 7/2010 | Hami et al. |
| D619,694 S | 7/2010 | Hami et al. |
| D620,573 S | 7/2010 | Hami et al. |
| D622,835 S | 8/2010 | Mendheim |
| 7,780,094 B2 | 8/2010 | Caserta et al. |
| D625,798 S | 10/2010 | Hami et al. |
| D629,881 S | 12/2010 | Valentino et al. |
| D631,534 S | 1/2011 | Kajizuka |
| D631,954 S | 2/2011 | Bertassi et al. |
| D633,610 S | 3/2011 | Wu |
| D637,275 S | 5/2011 | Baraky |
| D640,358 S | 6/2011 | Irvin |
| D642,668 S | 8/2011 | Lablaine |
| D645,949 S | 9/2011 | Brandenburg et al. |
| D647,186 S | 10/2011 | Chan et al. |
| D649,237 S | 11/2011 | Bilko et al. |
| D650,892 S | 12/2011 | Wheatley |
| 8,147,761 B2 | 4/2012 | Wheatley et al. |
| D660,950 S | 5/2012 | Finlay |
| D662,581 S | 6/2012 | Savegnago |
| 8,197,761 B1 | 6/2012 | Miller-Larry |
| 8,251,299 B1 | 8/2012 | Irvin |
| 8,485,454 B1 | 7/2013 | Irvin |
| 8,490,846 B1 | 7/2013 | Wheatley |
| 2003/0097936 A1 | 5/2003 | Maleeny et al. |
| 2003/0199421 A1 | 10/2003 | Copfer |
| 2004/0265164 A1 | 12/2004 | Woo et al. |
| 2005/0127538 A1 | 6/2005 | Fabrega et al. |
| 2005/0169793 A1 | 8/2005 | Wheatley et al. |
| 2006/0043216 A1 | 3/2006 | Robinson |
| 2006/0078477 A1 | 4/2006 | Althouse et al. |
| 2006/0196964 A1 | 9/2006 | Wheatley et al. |
| 2006/0279008 A1 | 12/2006 | Jursich |
| 2007/0057084 A1 | 3/2007 | Vieira |
| 2007/0160492 A1 | 7/2007 | Spector |
| 2007/0290064 A1 | 12/2007 | Majerowski et al. |
| 2008/0099576 A1 | 5/2008 | Hart |
| 2008/0128925 A1 | 6/2008 | Pankhurst et al. |
| 2009/0004420 A1 | 1/2009 | Wheatley |
| 2009/0010813 A1 | 1/2009 | Wang et al. |
| 2009/0072045 A1 | 3/2009 | Wheatley et al. |
| 2009/0173799 A1 | 7/2009 | Litten-Brown et al. |
| 2009/0212124 A1* | 8/2009 | Kenny ............... 239/58 |
| 2010/0010409 A1 | 1/2010 | Irvin |
| 2010/0019059 A1 | 1/2010 | Bulsink et al. |
| 2010/0065654 A1 | 3/2010 | Wheatley et al. |
| 2010/0187327 A1 | 7/2010 | Irvin |
| 2010/0288847 A1 | 11/2010 | Gruenbacher et al. |
| 2011/0110823 A1 | 5/2011 | Wheatley et al. |
| 2012/0076276 A1 | 3/2012 | Wang et al. |

FOREIGN PATENT DOCUMENTS

| | | |
|---|---|---|
| EP | 1 346 734 | 9/2003 |
| WO | WO 00/24434 | 5/2000 |
| WO | WO 00/64498 | 11/2000 |
| WO | WO 02/35975 | 5/2002 |
| WO | WO 02/38029 | 5/2002 |
| WO | WO 2006/010282 | 2/2006 |
| WO | WO 2006/084160 | 8/2006 |
| WO | WO 2004/078219 | 1/2007 |

OTHER PUBLICATIONS

U.S. Appl. No. 13/282,035, filed Oct. 26, 2011, Nathaniel Finlay, office action dated Apr. 17, 2013.

U.S. Appl. No. 12/987,662, filed Jan. 10, 2011; Alan J. Wheatley, notice of allowance dated Jun. 7, 2013.

U.S. Appl. No. 12/979,690, filed Dec. 28, 2010; Alan J. Wheatley, notice of allowance dated Jun. 10, 2013.

U.S. Appl. No. 12/979,601, filed Dec. 28, 2010; Alan J. Wheatley, notice of allowance dated Jun. 10, 2013.

U.S. Appl. No. 29/435,391; filed Oct. 23, 2012; Aaron Irvin, notice of allowance dated Jun. 18, 2013.

about.com Housekeeping, http://housekeeping.about.com/od/pr...af-fresh, Febrezee Noticeables, accessed Oct. 2, 2008, 2 pages.

Aromate E-News, Innovation in Novelty Fragrance, Http://209.85.173.104/seasrch?qcach . . . , accessed Oct. 8, 2008, 2 pages.

ecrater, www.ecrater.com/product.hp?. . . , Yankee Candle Selects Two Scents Electric Fragrance Unit Macintosh/Home Sweet Home, accessed Oct. 2, 2008, 1 page.

http://decomodo.com/articles/categor/lighting/, Bamboo Pillar Candle, Jan. 8, 2008, 1 page.

http://shop.advanceautoparts.com/webapp/wcs/stores/servlet/product_6170795-P_N3004 . . . Advance Auto Part; Arometrics Dual-Scent Vent—Juicy Strawberry and Vanilla; 1 Page; accessed Dec. 10, 2010.

http://www.bestliquidations.com/Medo_Vent Frehser.htm; BestLiquidations.com; Medo Vent Fresh Air Fresheners; 2 pages; accessed Dec. 10, 2010.

Medo® Air Fresheners; Auto Expressions™ 2005 Product Catalog; 25 pages.

Pictures (3) of Medo® auto Expressions Vent™ Air Freshener distributed by SOPUS Products of Moorpark, CA 2003 copyright date on package.

Scents & Sprays, www.scentsandsprays.com/ya . . . , Yankee Autumn Bounty Electric 2 Home Air Fresheners, copyright 2001-2008 scentsandsprays.com, accessed Oct. 2, 2008, 1 page.

www.4imprint.com/EXEC/DETAIL/FROMPRODUCT-GROUP/~SKU100300/~CA100300.htm, Hot Rod Vent Stick Air Freshener (it . . . , accessed Aug. 12, 2008, 2 pages.

www.autothing.com/Products/Air%20Fresheners/air%20freshener-clip.htm, Air Fresheners, Fresh Scents for you mobile Life, Clip-on Air Vent Clips rom Eagle o., Accessed Aug. 12, 2008, 1 page.

www.chicscents.com/Products.aspx Island Adventure Sandals; 2 pages; accessed Feb. 1, 2011.

www.chicscents.com/Products.aspx; Inspiration 3-D by Chic; 2 pages; accessed Feb. 1, 2011.

U.S. Appl. No. 12/979,763, filed Dec. 28, 2010, Aaron Irvin.

U.S. Appl. No. 12/979,795, filed Dec. 28, 2010, Aaron Irvin.

U.S. Appl. No. 12/979,813, filed Dec. 28, 2010, Aaron Irvin.

U.S. Appl. No. 13/191,966, filed Jul. 27, 2011, Aaron Irvin.

U.S. Appl. No. 12/979,763, filed Dec. 28, 2010, Aaron Irvin, office action dated Dec. 14, 2012.

U.S. Appl. No. 12/693,543, filed Jan. 26, 2010, Aaron Irvin, office action dated Dec. 18, 2012.

U.S. Appl. No. 13/009,574, filed Jan. 19, 2011, Alan J. Wheatley, office action dated Jan. 11, 2013.

U.S. Appl. No. 12/979,795, filed Dec. 28, 2010, Aaron Irvin, office action dated Jan. 28, 2013.

U.S. Appl. No. 12/979,813, filed Dec. 28, 2010, Aaron Irvin, office action dated Jan. 31, 2013.

U.S. Appl. No. 12/915,983, filed Oct. 29, 2010, Alan J. Wheatley, notice of allowance dated Feb. 20, 2013.

U.S. Appl. No. 29/435,389, filed Oct. 23, 2012, Aaron Irvin, notice of allowance dated Mar. 1, 2013.

U.S. Appl. No. 12/979,690, filed Dec. 28, 2010, Alan J. Wheatley, office action dated Mar. 1, 2013.

U.S. Appl. No. 12/987,662, filed Jan. 10, 2011, Alan J. Wheatley, office action dated Mar. 21, 2013.

(56) References Cited

OTHER PUBLICATIONS

U.S. Appl. No. 12/979,601, filed Dec. 28, 2010, Alan J. Wheatley, office action dated Mar. 1, 2013.
U.S. Appl. No. 13/009,574, filed Jan. 19, 2011, Alan J. Wheatley, notice of allowance dated Apr. 3, 2013.
U.S. Appl. No. 13/359,726, filed Jan. 27, 2012, Aaron Irvin, office action dated Apr. 5, 2013.
U.S. Appl. No. 13/282,035, filed Oct. 26, 2011, Nathaniel Finlay, office action dated Jul. 17, 2013.
U.S. Appl. No. 12/979,795, filed Dec. 28, 2010, Aaron Irvin, office action dated Oct. 18, 2013.
U.S. Appl. No. 13/940,074, filed Jul. 11, 2013, Alan J. Wheatley, office action dated Nov. 20, 2013.
U.S. Appl. No. 12/915,924, filed Oct. 29, 2010, Nathaniel Finlay, notice of allowance dated Nov. 22, 2013.
U.S. Appl. No. 13/282,035, filed Oct. 26, 2011, Nathaniel Finlay, notice of allowance dated Nov. 26, 2013.
U.S. Appl. No. 13/281,890, filed Oct. 26, 2011, Aaron Irvin, notice of allowance dated Dec. 10, 2013.

* cited by examiner

AIR FRESHENER CANISTER WITH PULL TOP

PRIORITY CLAIM

Priority is claimed to U.S. Provisional Patent Application Ser. No. 61/584,917, filed Jan. 10, 2012, which is hereby incorporated herein by reference in its entirety.

BACKGROUND

1. Field of the Invention

The present invention relates generally to air fresheners.

2. Related Art

Some air fresheners include a scented material in a can with a removable top. A removable cap with holes is disposed on the can and over the removable top. To use, the cap is removed, the removable top is removed from the can and discarded, and the cap is replaced on the can. The cap with holes allows fragrance from the can, while providing some protection to the scented material. One problem with this design is that the cap can become separated from the can during shipping and handling, resulting in the loss of protection. In addition, the cap can become separated from the can during use. For example, the cap is easily removed by a child.

SUMMARY OF THE INVENTION

It has been recognized that it would be advantageous to develop an air freshener that resists tampering, improves safety, facilitates use, and stays together or retains its components. It has been recognized that it would be advantageous to develop an air freshener that includes a grid or control top that is secured in a canister to resist unintended or undesired removal and/or loss.

The invention provides an air freshener with a canister having an open top. A lid is secured to the open top of the canister to form a sealed container. A pull top is releasably secured to an aperture in the lid and forms a portion of the lid and the sealed container. A fragrant material is disposed in the canister and sealed in the sealed container. A grid or louver is disposed over the fragrant material and in the canister. The grid or louver is sealed in the sealed container between the fragrant material and the lid. The grid or louver maintains the fragrant material in the canister when the pull top is removed.

In addition, the invention provides an air freshener with a canister having a bottom wall, a side wall and an open top. A fragrant material is disposed in the canister and capable of releasing a desired fragrance. The fragrant material includes a fibrous material impregnated with the desired fragrance or a gel with the desired fragrance. A lid is secured to the open top of the canister to form a sealed container. The lid includes an annular outer portion with an outer perimeter fixed to the canister and an inner perimeter defining an aperture. A pull top has an outer perimeter releasably secured to the inner perimeter of the outer portion and extends over the aperture in the lid and forms a portion of the lid and the sealed container. The pull top has a tab pullable to separate the pull top from the lid. The pull top has an upper surface forming an exposed surface when secured to the canister. A grid with holes therein is disposed in the canister and is disposed over the fragrant material and below the pull top. The grid is thus contained inside the container when the pull top is secured to the lid. The grid has an upper surface forming an exposed surface when the pull top is separated from the lid. The grid retains the fragrant material in the canister when the pull top is separated from the lid. The grid includes a stand disposed in the canister below the pull top. The stand has a platform disposed below the pull top with a plurality of platform openings therein. The stand has a plurality of legs supporting the platform above the bottom wall of the canister. The stand has a center axle hole and a plurality of perimeter slots. A dial is pivotally disposed on the stand and below the pull top. The dial has a central axle received in the axle hole of the stand. The dial has a plurality of perimeter fingers each received in a different one of the plurality of perimeter slots of the stand. The dial has a plurality of dial openings selectively alignable with the plurality of platform openings of the stand. The dial and the stand, with the respective plurality of dial openings and the plurality of stand openings, define a scent control lid disposed over the fragrant material and below the pull top, and thus contained inside the container when the pull top is secured to the canister, and exposed when the pull top is separated from the canister.

Furthermore, the invention provides an air freshener with a canister having an open top. A fragrant material including a desired fragrance is carried by a carrier and disposed in the canister. A grid is disposed in and fixedly secured to the canister and over the fragrant material. A pull top is releasably secured to the canister and extends over the open top to form a sealed container containing the fragrant material and the grid. The pull top is selectively removable from the canister to expose the grid therein and allow release of the desired fragrance through the grid.

BRIEF DESCRIPTION OF THE DRAWINGS

Additional features and advantages of the invention will be apparent from the detailed description which follows, taken in conjunction with the accompanying drawings, which together illustrate, by way of example, features of the invention; and, wherein.

Reference will now be made to the exemplary embodiments illustrated, and specific language will be used herein to describe the same. It will nevertheless be understood that no limitation of the scope of the invention is thereby intended.

DETAILED DESCRIPTION OF EXAMPLE EMBODIMENT(S)

Definitions

The term "scent material" and "fragrant material" are used interchangeably herein to refer broadly to a material that carries a desired fragrance or scent, or even a neutralizing agent. The fragrant material or scent material can include a desired fragrance carried by a carrier, such as a fibrous material impregnated with the desired fragrance, or a gel with the desired fragrance.

Description

As illustrated in the FIGS. 1-18, an air freshener, indicated generally at 10, in an example implementation in accordance with the invention is shown. The air freshener can provide a desired and/or aesthetically pleasing scent, fragrance, aroma or neutralizing agent. Such an air freshener can be used in vehicles, lockers, etc. The air freshener can include a fragrant material 22 sealed in a sealed container formed by a canister 18 and a lid or pull top 26. In addition, a grid or louver 14, or a scent control top, or the like, can also be sealed in the container under the lid or pull top, as opposed to on top of the pull top. Thus, the grid, louver or scent control top is secured with the air freshener or canister to resist unintended separation from the air freshener or canister. The grid, louver or scent control top can be secured to the canister to maintain the fragrant material, or carrier thereof, in the canister, and/or to resist tampering with the fragrant material, or carrier thereof. The grid, louver or scent control top can be retained by the lid or portion thereof, or a portion of the pull tab.

Figure 14:
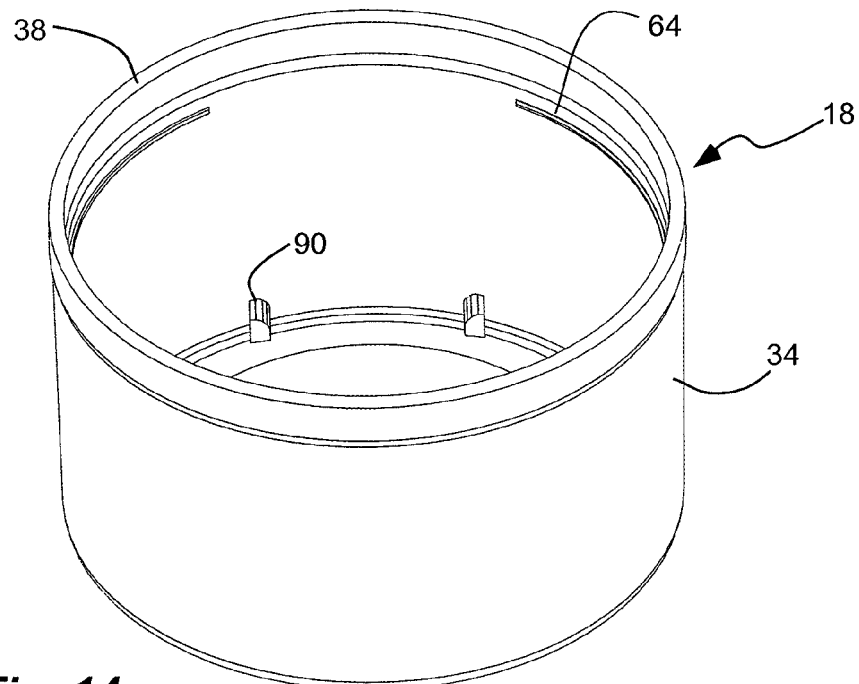
FIG. 14 is a perspective view of a container of the air freshener of FIG. 1.
Figure 15:
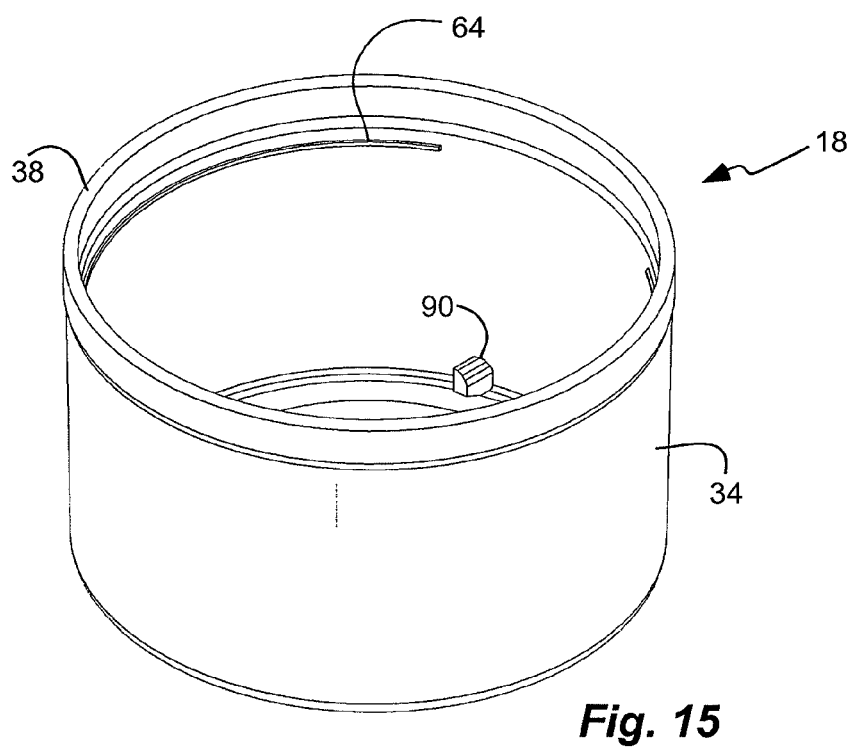
FIG. 15 is a perspective view of the container of FIG. 14.
Figure 16:
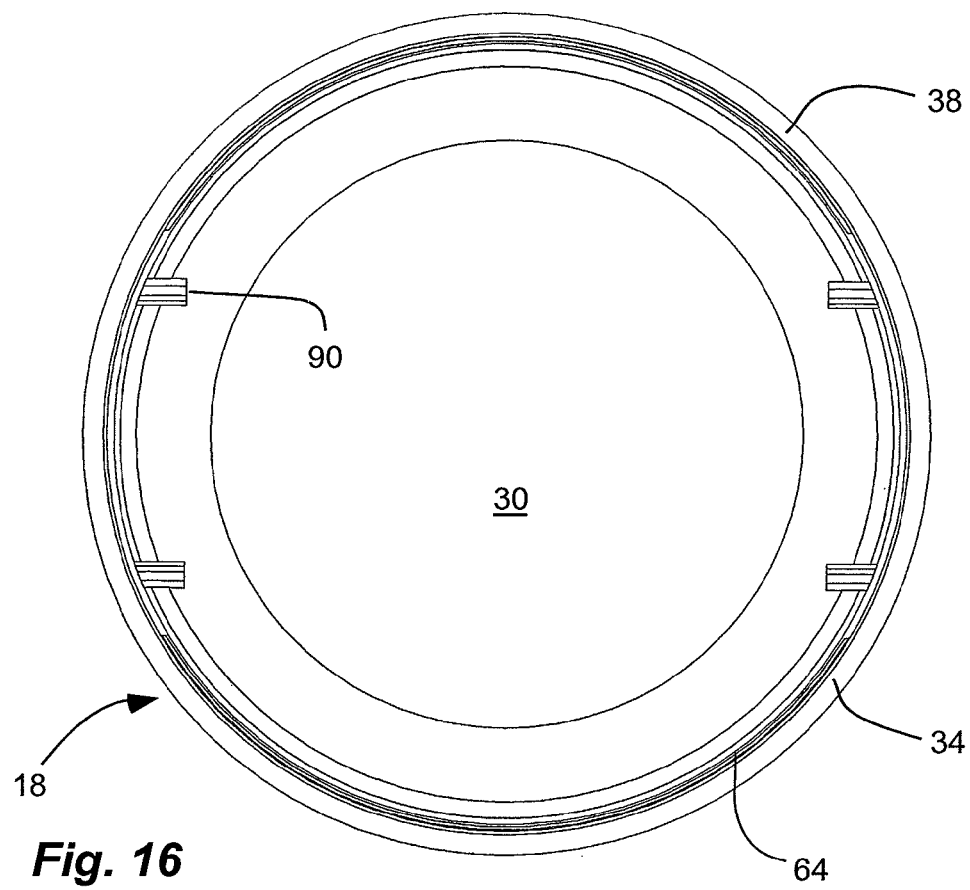
FIG. 16 is a top view of the container of FIG. 14.
Figure 17:
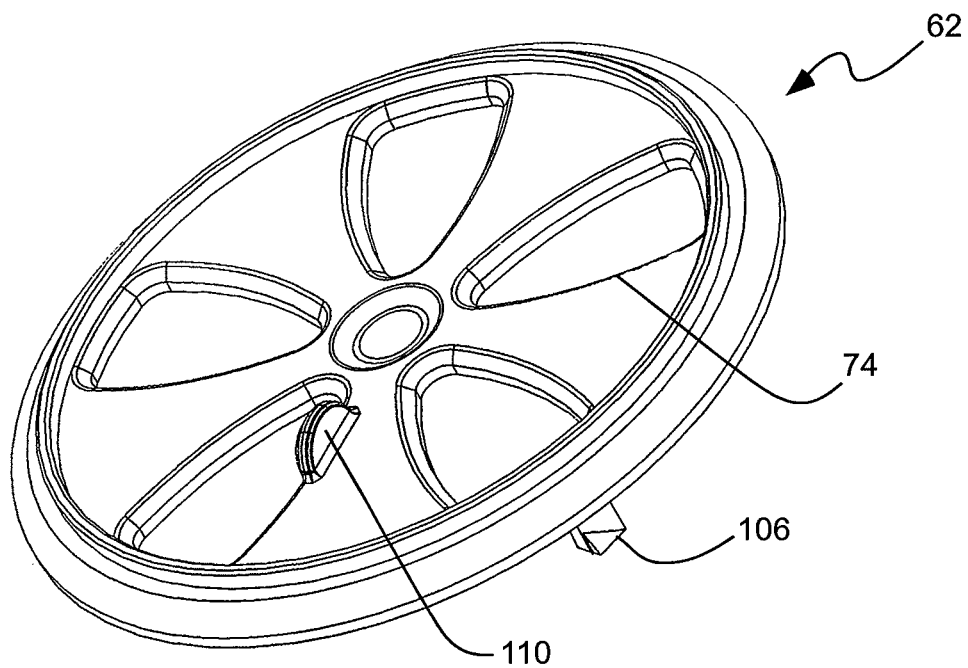
FIG. 17 is a perspective view of a dial of the air freshener of FIG. 1.
Figure 18:
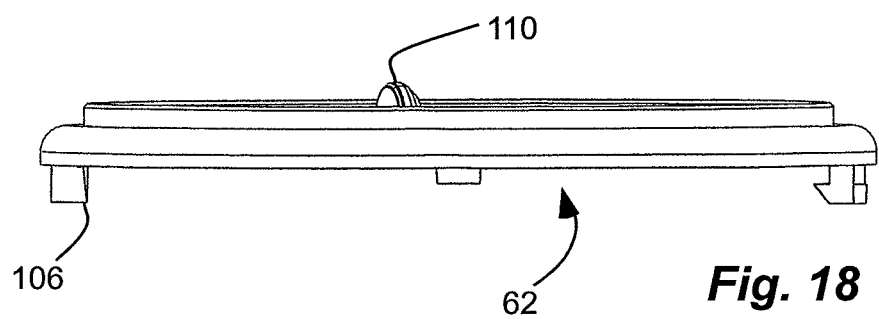
FIG. 18 is a side view of the dial of FIG. 17.

The canister 18 can have a bottom wall 30, a perimeter side wall 34 and an open top 38 (FIGS. 14 and 15). The canister 18 and the side wall 34 can be cylindrical. The canister can be formed from metal or plastic. For example, the canister, and the bottom and side walls, can be integrally formed at the same time with plastic by injection molding or vacuum molding. As another example, the canister, and the bottom and side walls, can be integrally formed at the same time with metal by stamping. The perimeter side wall can be slightly tapered so that the canister has a greater diameter near the open top, and a lesser diameter at the bottom. In addition, the bottom wall can be indented forming a perimeter annular channel around a bottom of the canister between the side wall and the bottom wall. The air freshener can be configured to be placed on a support surface that is horizontal with the bottom wall disposed on the support surface.

A fragrant material 22 (FIG. 3) is disposed in the canister 18 and capable of releasing a desired fragrance through the open top 38 of the canister and through the grid 14, as discussed in greater detail below. The fragrant material can include a desired fragrance carried by a carrier. For example, the fragrant material can include a fibrous material impregnated with the desired fragrance, or a gel with the desired fragrance. The fragrant material can be configured to release the fragrance over time. The fragrant material or fragrance can include an oil.

The open top 38 of the canister 18 can be sealed by the pull top 26 and/or lid to form a sealed container containing the fragrant material 22 and the grid 26. Thus, the canister and the pull top 26 and/or lid can form a hollow therein container the fragrant material and the grid. The sealed container resists premature release of the fragrance, and/or premature drying of the fragrant material. The pull top 38 can re releasably secured to the open top 38 of the canister 18. The pull top 26 can have a tab 42 pullable to separate the pull top from the canister. The pull top can have an upper surface forming an exposed surface when secured to the canister. In one aspect, the pull top 26 can be directly coupled to the open top 38 of the canister 18, such as with a releasable adhesive, or a mechanical interference or press fit. In another aspect, the pull top 26 can be indirectly coupled to the open top 38 of the canister 18, such as by a lid 44. The sealed container can be formed by the canister and the pull tab and lid (or inner and outer portions thereof).

Figure 1:
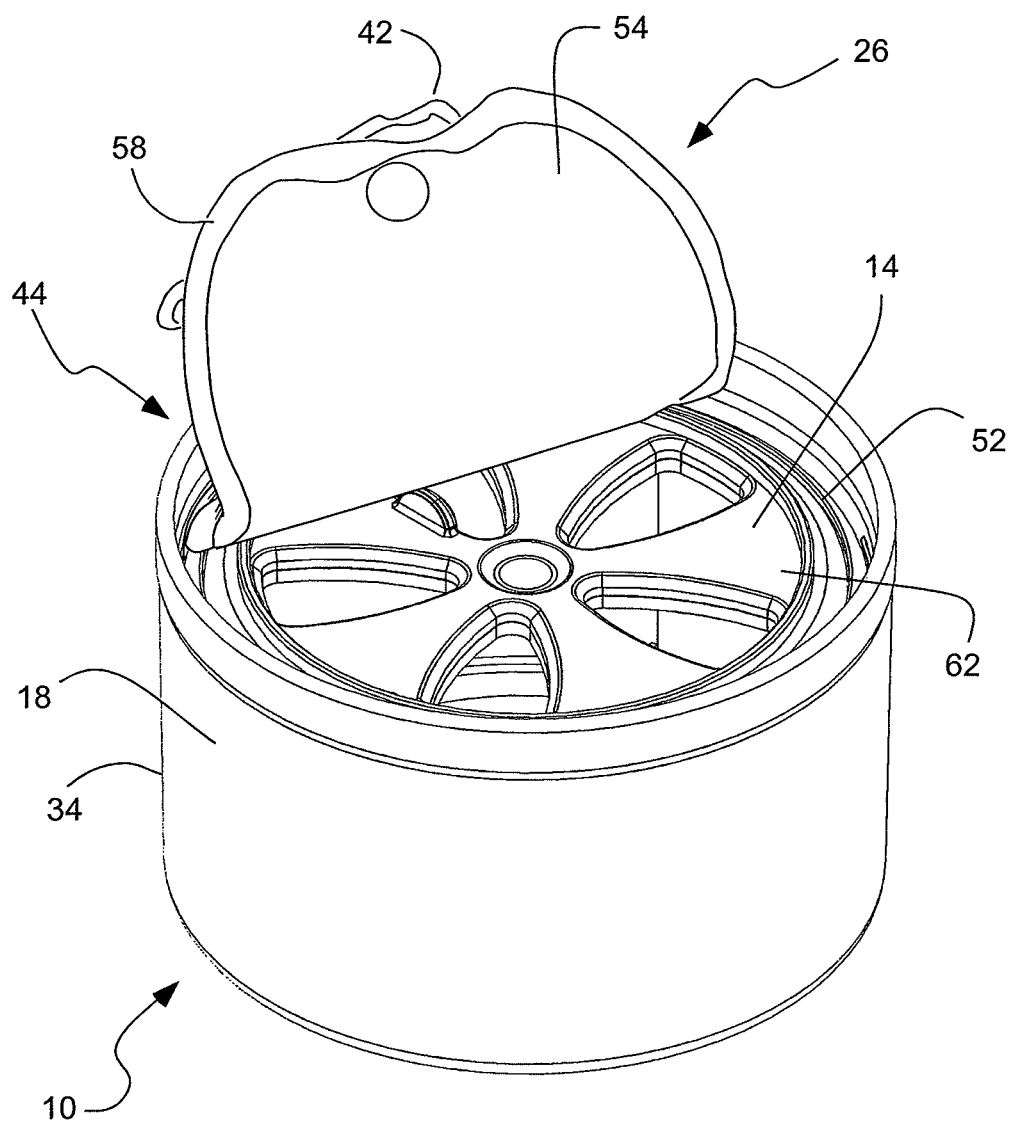
FIG. 1 is a perspective view of an air freshener in accordance with an embodiment of the present invention, shown with a pull top partially separated from a lid and/or canister.
Figure 2:
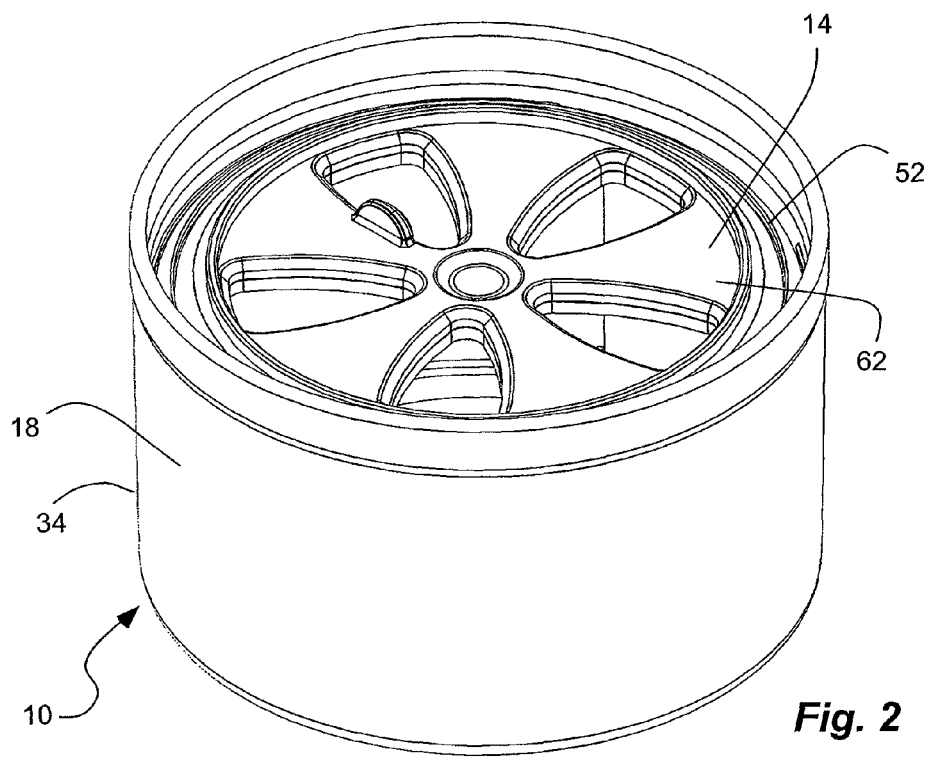
FIG. 2 is a perspective view of the air freshener of FIG. 1, shown with the pull top and/or lid removed.
Figure 3:
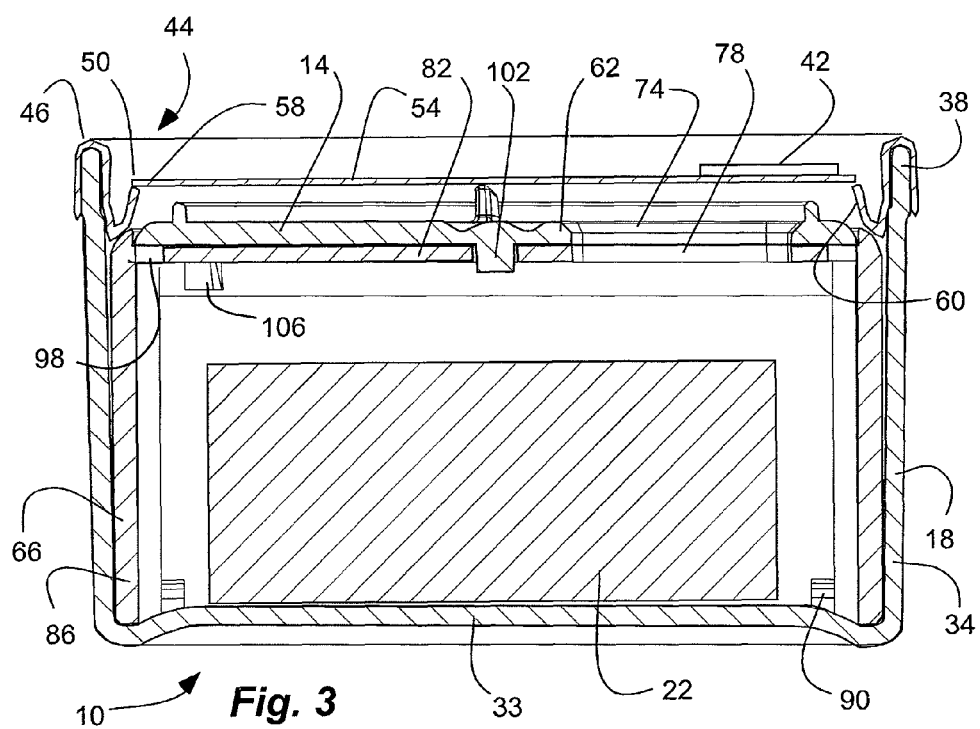
FIG. 3 is a cross-sectional side view of the air freshener of FIG. 1, shown with the pull top and/or lid in a closed or sealed configuration forming a sealed container.
Figure 4:
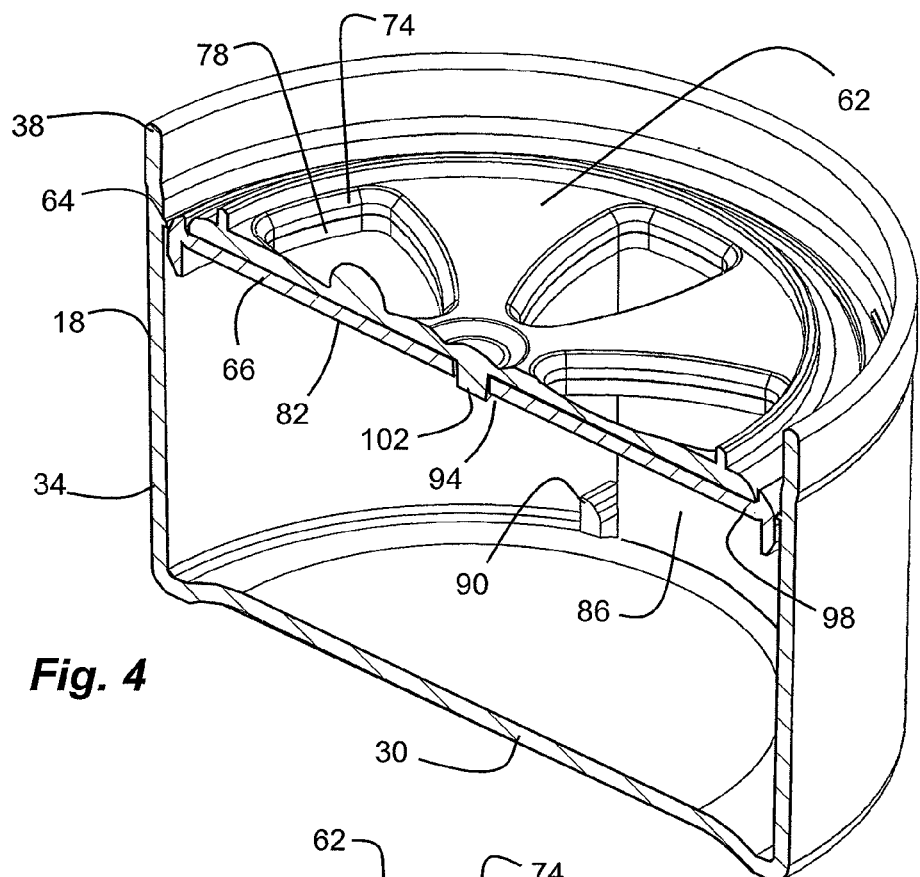
FIG. 4 is a cross-sectional perspective view of the air freshener of FIG. 1 taken along line 4-4 of FIG. 10, shown with the pull top and/or lid removed.
Figure 5:
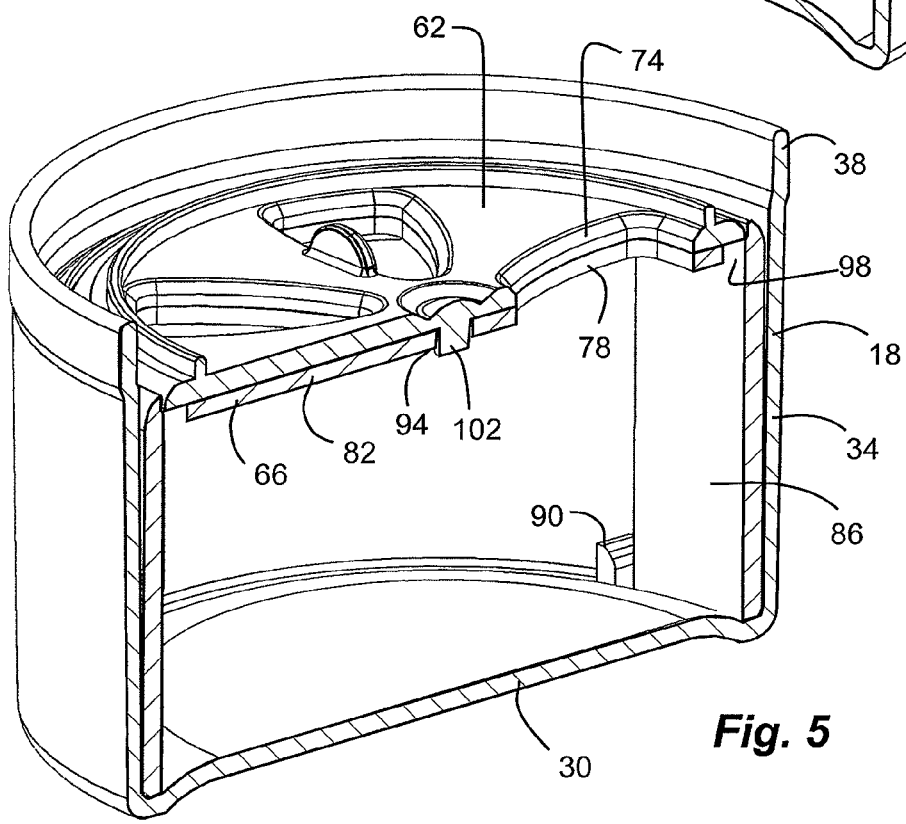
FIG. 5 is a cross-sectional perspective view of the air freshener of FIG. 1 taken along line 5-5 of FIG. 10, shown with the pull top and/or lid removed.
Figure 6:
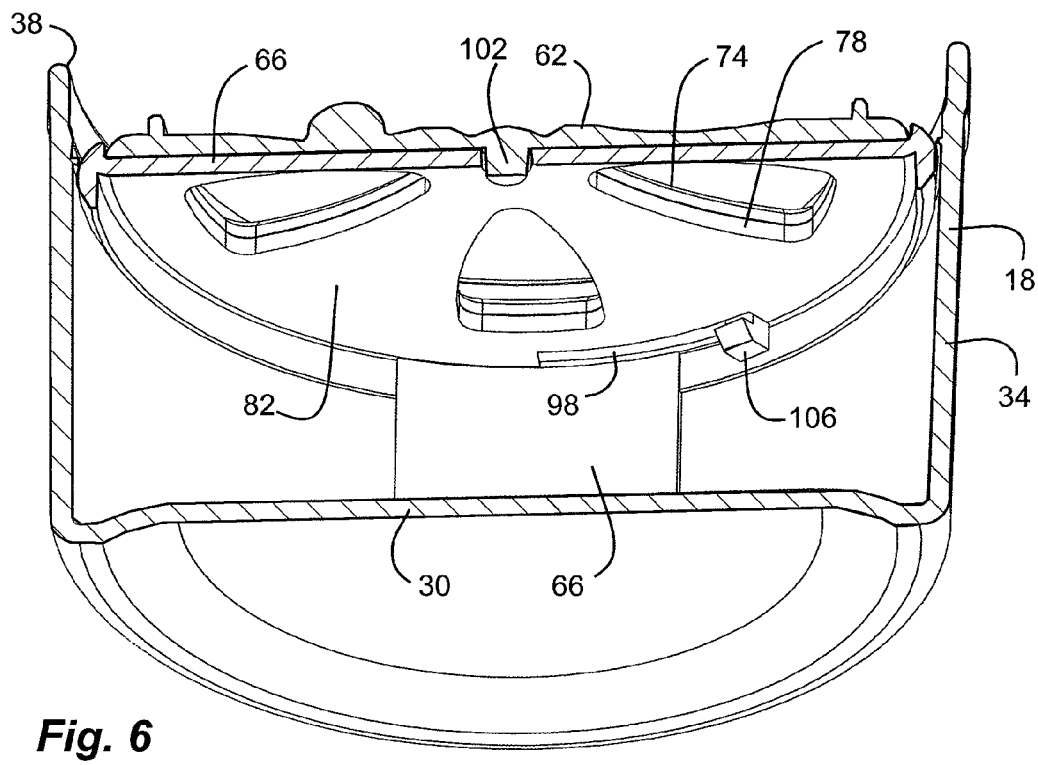
FIG. 6 is a cross-sectional perspective view of the air freshener of FIG. 1 taken along line 4-4 of FIG. 10, shown with the pull top and/or lid removed.
Figure 7:
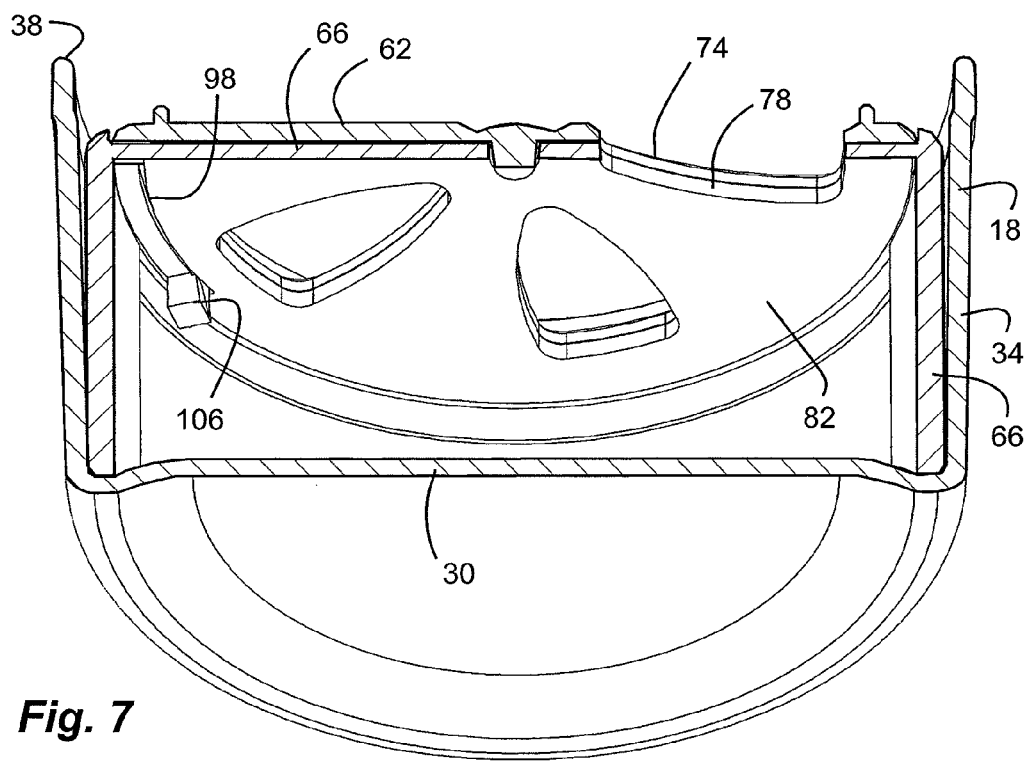
FIG. 7 is a cross-sectional perspective view of the air freshener of FIG. 1 taken along line 5-5 of FIG. 10, shown with the pull top and/or lid removed.
Figure 8:
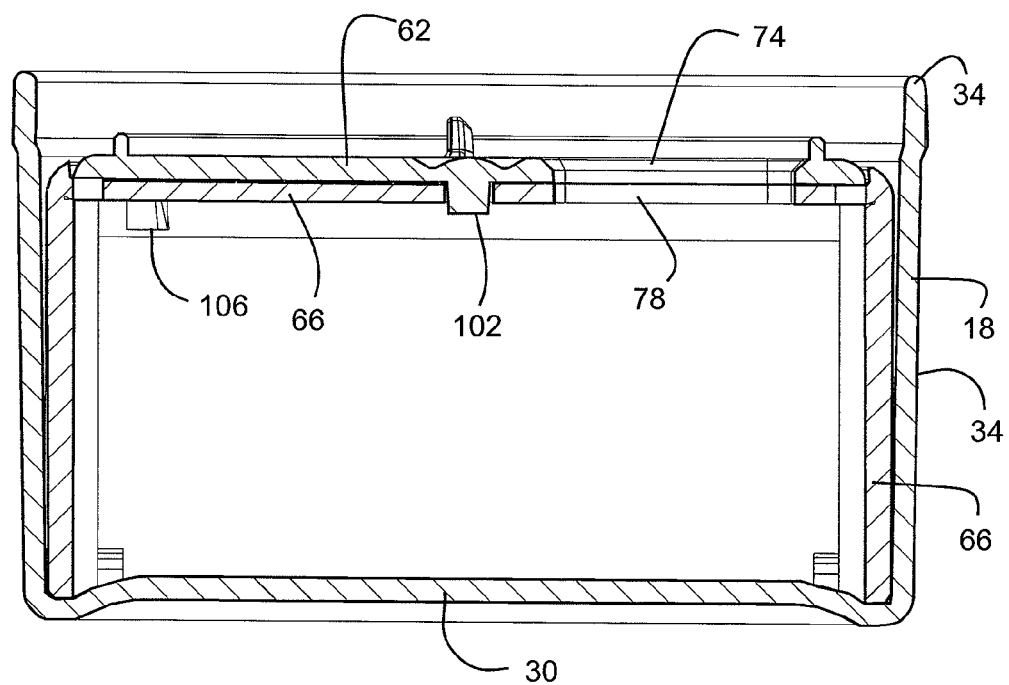
FIG. 8 is a cross-sectional perspective view of the air freshener of FIG. 1 taken along line 5-5 of FIG. 10, shown with the pull top and/or lid removed.
Figure 9:
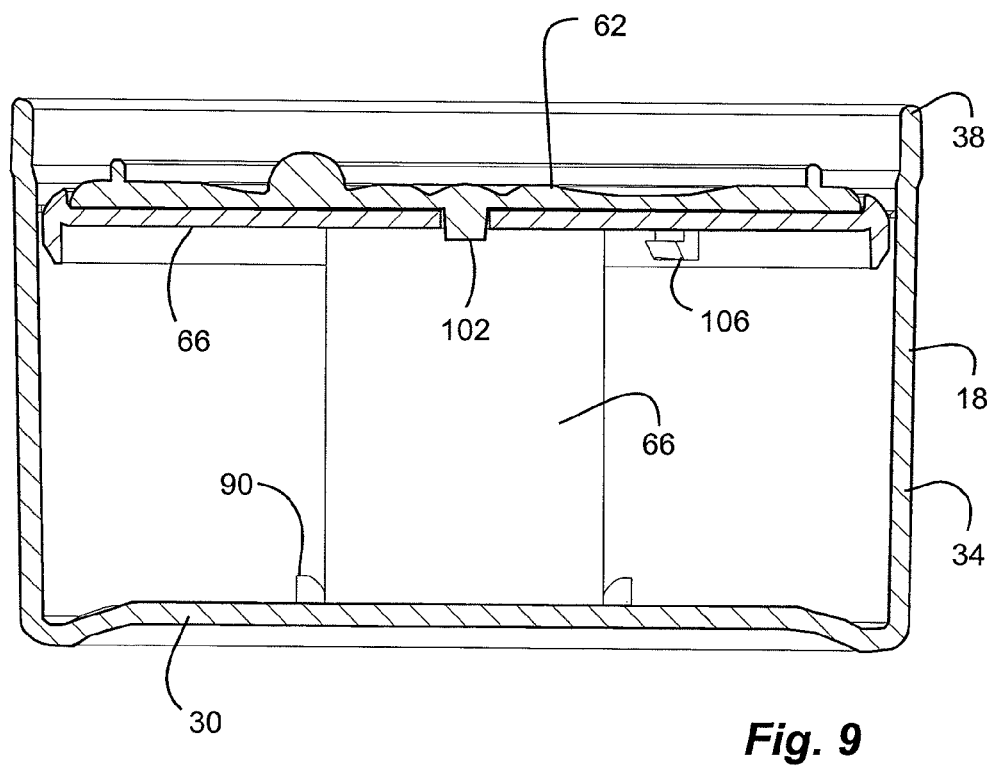
FIG. 9 is a cross-sectional perspective view of the air freshener of FIG. 1 taken along line 4-4 of FIG. 10, shown with the pull top and/or lid removed.
Figure 10:
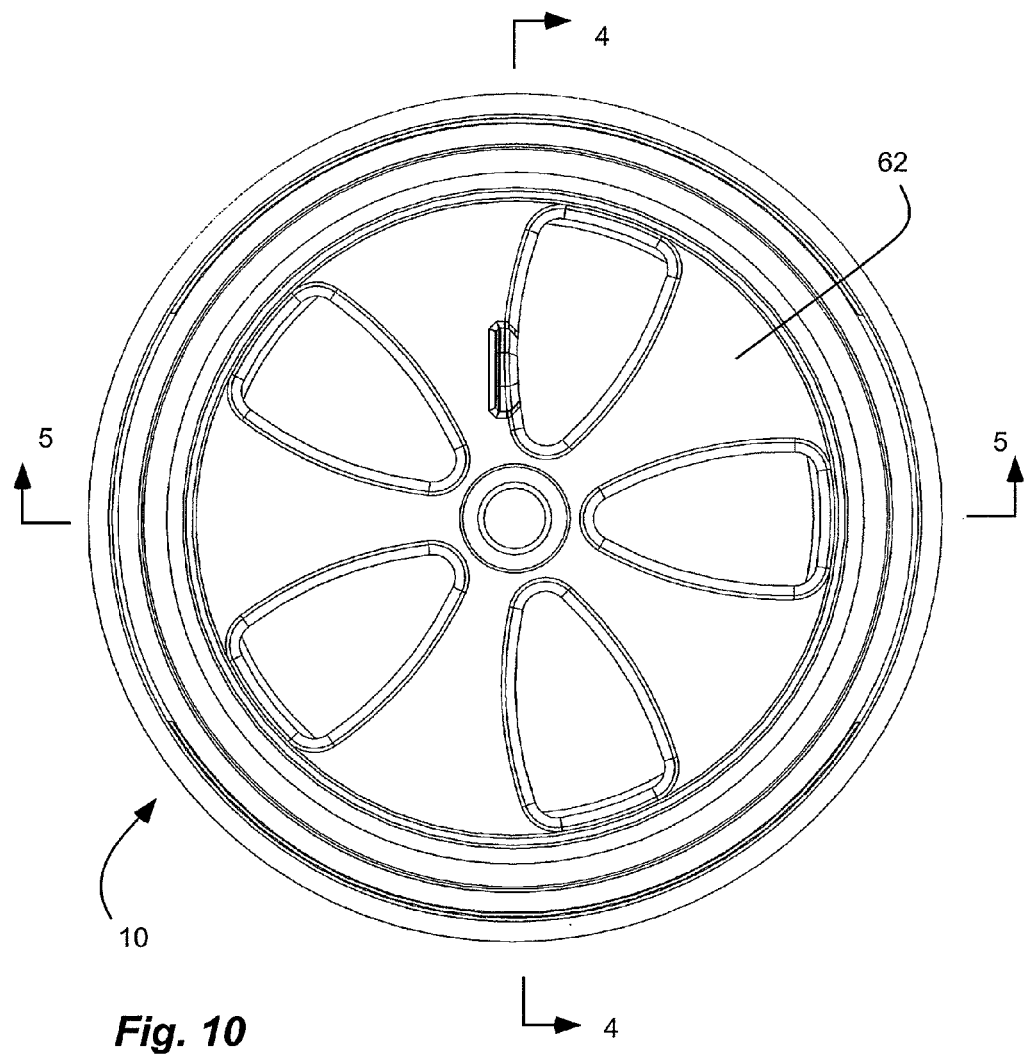
FIG. 10 is a top view of the air freshener of FIG. 1, shown with the pull top and/or lid removed.

The pull top 26 can include or can be a portion of the lid 44 that can be secured to the open top 38 of the canister 18. The lid 44, or the pull top 26, can include an annular outer portion 46 (FIG. 3) with an outer perimeter fixed to the canister 18, and an inner perimeter 50 defining an aperture 52 (FIG. 1). The pull top 26 can also include an inner portion 54 spanning the aperture 52 of the outer portion 46, and having an outer perimeter 58 releasably secured to the inner perimeter 50 of the outer portion 46. Thus, in use, a user can lift the tab 42, which can be secured to the pull top and positioned such that lifting one end of the tab creates a lever to that the other end pivots downward against an interface or seam between the inner and outer portions, and causing the inner and outer portions to separate at the tab; and then continue to lift the tab pulling the inner portion from the outer portion along the interface or seam. The lid 44 and/or the pull top 26, and the outer portion 46 and the inner portion 54 thereof, can be formed of metal or foil, a plastic, or a combination or laminate of both. The outer portion 46 can be bent or formed around the upper end or open top 38 of the side wall 34 of the canister 18. The inner portion 54 of the pull top 26 can be formed by stamping to create a frangible interface or seam between the inner and outer portions. Alternatively, the inner portion can be adhered to the outer portion along the interface or seam. Alternatively, the pull top 26 can be a metal or plastic foil adhered to the upper end of the side wall of the canister. Alternatively, the pull top can be a metal or plastic foil mechanically formed around the upper end of the side wall of the canister. All or a portion of the pull top can separate from the canister. The annular outer portion 46 of the pull top can remain affixed to the canister and can extend radially inwardly to form a flange 60 (FIG. 3) to retain the grid in the canister. In addition, the canister 18 can have an inner lip 64 projecting inwardly on an interior of the canister neat a top thereof, and over the grid to retain the grid in the canister. The lip can extend entirely or partially around the interior of the canister, or may include multiple lip segments.

As described above, the air freshener 10 can include a grid or louver 14, or a scent control top, or the like, disposed over and/or across the opening or open top 38 of the canister 18 to retain the fragrant material 22 in the canister and resist tampering with and/or contact with the fragrant material. The grid 14 is disposed in the canister 18, and in the sealed container formed by the canister 18 and the pull top 26 and/or lid 44. Thus, the grid 14 is disposed under the pull top 26 when the pull top is secured over the canister. Thus, the grid 14 remains inside the canister and container until use, unlike prior art air fresheners with a cap disposed over the canister and separable from the canister prior to use. In addition, the grid 14 can have an outer diameter or size greater than the aperture 52 in the lid 44 to retain the grid 14 in the canister even after the pull top is removed. Thus, the aperture 52 is smaller than the grid 14 so that a perimeter or flange 60 of the lid 44 extends over canister and the grid. Thus, the grid is fixedly secured to the or in the canister and over the fragrant material. The grid 14 or louver, or the scent control top, can include a plurality of holes or apertures to allow the fragrance to escape during use, after the pull top has been removed or separated from the canister. The grid thus has an upper surface forming an exposed surface when the pull top is separated from the lid.

Figure 11:
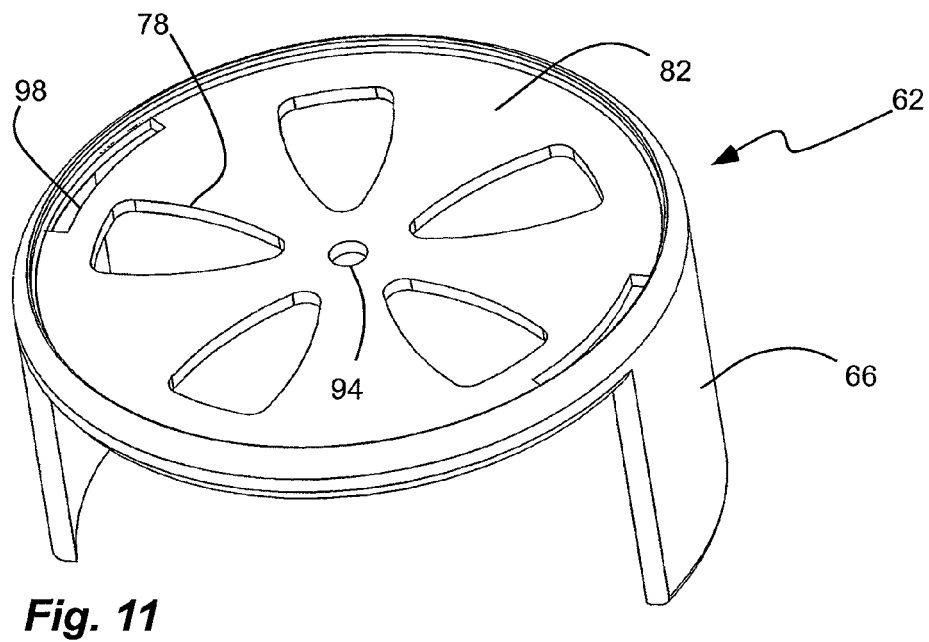
FIG. 11 is a perspective view of a stand of the air freshener of FIG. 1.
Figure 12:
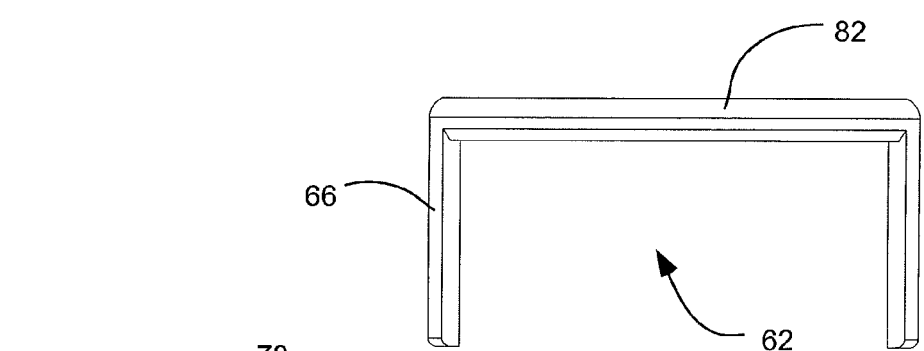
FIG. 12 is a side view of the stand of FIG. 11.
Figure 13:
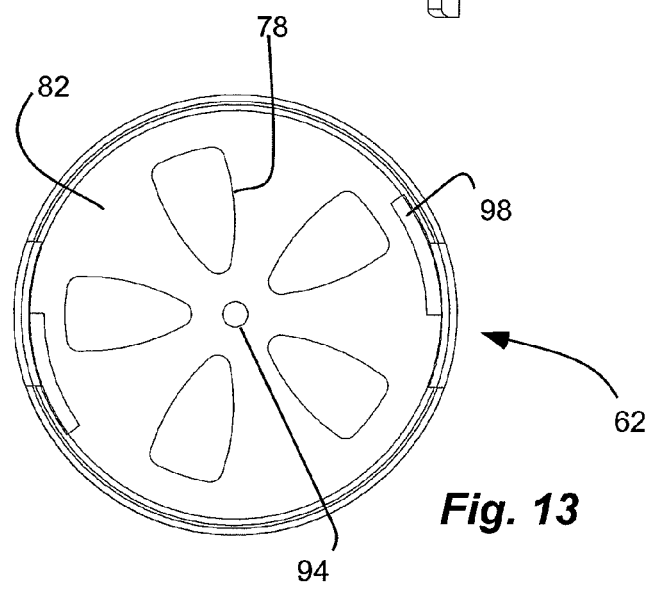
FIG. 13 is a top view of the stand of FIG. 11.

The grid can include a stand 66 disposed in the canister 18 below the pull top 26 and standing on the bottom wall 30 of the canister. The stand 66 can have a platform 82 also disposed below the pull top 26 with a plurality of legs 86 supporting the platform above the bottom wall 30 of the canister. The stand 66 or platform 82 can have a plurality of platform or stand openings or holes 78 therein. The stand holes can be arrayed about a center or longitudinal axis, and thus can circumscribe the center or longitudinal axis. In addition, the stand 66 can have a center axle hole 94 and a plurality of perimeter slots 98, as shown in FIG. 11. The canister 18 can have a pair of stops 90 formed on the bottom wall 3 of the canister and on opposite sides of a leg 86 of the plurality of legs 86 to resist pivoting of the stand (along with a dial as described below). The stand can be formed of plastic and inserted into the canister after the scent material, and before the lid is disposed on the canister.

In addition, the grid 14 can include a dial 62 pivotally carried by, and disposed on, the stand 66 or the platform 82 thereof. The dial 62 is pivotally disposed on the stand 66 or platform, and below the pull top 26. The dial 62 can have a plurality of dial openings or holes 74. The dial holes 74 can be arrayed about a center or longitudinal axis, and thus can circumscribe the center or longitudinal axis. The dial holes 74 can be selectively alignable or misalignable with the stand holes 78 to open, close, and/or partially close the grid. The dial and stand can also have solid portions between the holes so that the holes of one can be aligned with the solid portions of another to close the grid. The grid, or dial and stand portions thereof, can form a scent control lid.

The dial 62 can have a central axle 102 received in the axle hole 94 of the stand 66. Thus, the dial 62 can pivot with respect to the stand 66 or platform 82 about the axle 102 and axle hole 94 so selectively align or misalign the holes 74 and 78. In addition, the dial can have a plurality of perimeter fingers 106 each received in a different one of the plurality of perimeter slots 98 of the stand 66. Each of the plurality of fingers 106 can have an enlarged distal end press-fit through a different one of the plurality of perimeter slots of the stand. Thus, the enlarged distal ends of the fingers can secure the dial to the platform or stand. Furthermore, the dial 62 can have a tab 110 protruding from a top of the dial. The dial can be formed of plastic.

Alternatively, the dial can be provided with a axle hole and the stand or platform can be provided with an axle.

The dial 62 and the stand 66 with the respective plurality of dial openings and the plurality of stand openings define a scent control lid disposed over the fragrant material and below the pull top, and thus contained inside the container when the pull top is secured to the canister, and exposed when the pull top is separated from the canister.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The invention claimed is:

1. An air freshener device, comprising:
   a) a canister having a perimeter side wall and an open top;
   b) a lid secured to the open top of the canister to form a sealed container;
   c) a pull top releasably secured to an aperture in the lid and forming a portion of the lid and the sealed container;
   d) a fragrant material disposed in the canister and sealed in the sealed container;
   e) a grid or louver disposed over the fragrant material and in the canister, and sealed in the sealed container between the fragrant material and the lid, the grid or louver maintaining the fragrant material in the canister when the pull top is removed; and
   f) the grid or louver comprising a stand disposed in the canister below the lid, the stand having a platform disposed below the lid with a plurality of platform openings therein, the stand having a plurality of legs, inside the canister, at the perimeter side wall of the canister and supporting the platform above a bottom wall of the canister.

2. A device in accordance with claim 1, wherein the lid has a perimeter secured to the canister and the aperture is smaller than the grid or louver so that the perimeter of the lid extends over the canister and the grid or louver to maintaining the grid or louver in canister.

3. A device in accordance with claim 1, wherein the lid includes an annular outer portion with an outer perimeter fixed to the canister and an inner perimeter defining the aperture; wherein the pull top includes an inner portion spanning the aperture of the outer portion and having an outer perimeter releasably secured to the inner perimeter of the outer portion.

4. A device in accordance with claim 1, wherein the grid or louver further comprises:
   a dial pivotally disposed on the stand and below the lid, the dial having a plurality of dial openings selectively alignable with the plurality of platform openings of the stand.

5. A device in accordance with claim 1, further comprising:
   a pair of stops formed on the bottom wall of the canister and on opposite sides of a leg of the plurality of legs to resist pivoting of the stand along with the dial.

6. A device in accordance with claim 4, further comprising:
   a tab protruding from a top of the dial.

7. A device in accordance with claim 1, wherein the fragrant material includes a fibrous material impregnated with the desired fragrance or a gel with the desired fragrance.

8. A device in accordance with claim 1, wherein the grid or louver further comprises:
   a) the stand having a center axel hole and a plurality of perimeter slots;
   b) a dial pivotally disposed on the stand and below the lid, the dial having a central axel received in the axle hole of the stand, the dial having a plurality of perimeter fingers each received in a different one of the plurality of perimeter slots of the stand, the dial having a plurality of dial openings selectively alignable with the plurality of platform openings of the stand; and
   c) the dial and the stand with the respective plurality of dial openings and the plurality of stand openings defining a scent control top disposed over the fragrant material and below the lid, and thus contained inside the container when the pull top is secured to the canister, and exposed when the pull top is separated from the canister.

9. A device in accordance with claim 8, wherein each of the plurality of fingers has an enlarged distal end press-fit through a different one of the plurality of perimeter slots of the stand.

10. An air freshener device, comprising:
   a) a canister having a bottom wall, a side wall and an open top;
   b) a fragrant material disposed in the canister and capable of releasing a desired fragrance, the fragrant material including a fibrous material impregnated with the desired fragrance or a gel with the desired fragrance;
   c) a lid secured to the open top of the canister to form a sealed container, the lid including an annular outer portion with an outer perimeter fixed to the canister and an inner perimeter defining an aperture;
   d) a pull top having an outer perimeter releasably secured to the inner perimeter of the outer portion and extending over the aperture in the lid and forming a portion of the lid and the sealed container, the pull top having a tab pullable to separate the pull top from the lid, the pull top having an upper surface forming an exposed surface when secured to the canister;
   e) a grid with holes therein in the canister and disposed over the fragrant material and below the pull top, and thus contained inside the container when the pull top is secured to the lid, the grid having an upper surface forming an exposed surface when the pull top is separated from the lid, the grid retaining the fragrant material in the canister when the pull top is separated from the lid;
   f) the grid including a stand disposed in the canister below the pull top, the stand having a platform disposed below the pull top with a plurality of platform openings therein, the stand having a plurality of legs supporting the platform above the bottom wall of the canister, the stand having a center axle hole and a plurality of perimeter slots;
   g) a dial pivotally disposed on the stand and below the pull top, the dial having a central axle received in the axle hole of the stand, the dial having a plurality of perimeter fingers each received in a different one of the plurality of perimeter slots of the stand, the dial having a plurality of dial openings selectively alignable with the plurality of platform openings of the stand;
   h) the dial and the stand with the respective plurality of dial openings and the plurality of stand openings defining a scent control lid disposed over the fragrant material and below the pull top, and thus contained inside the container when the pull top is secured to the canister, and exposed when the pull top is separated from the canister; and
   i) a pair of stops formed on the bottom wall of the canister and on opposite sides of a leg of the plurality of legs to resist pivoting of the stand along with the dial.

11. A device in accordance with claim 10, wherein each of the plurality of fingers has an enlarged distal end press-fit through a different one of the plurality of perimeter slots of the stand.

12. An air freshener device, comprising:
   a) a canister having a perimeter side wall and an open top;
   b) a fragrant material including a desired fragrance carried by a carrier and disposed in the canister;
   c) a grid disposed in and fixedly secured to the canister and over the fragrant material;
   d) a pull top releasably secured to the canister and extending over the open top to form a sealed container containing the fragrant material and the grid, the pull top being selectively removable from the canister to expose the grid therein and allow release of the desired fragrance through the grid; and
   e) the grid comprising a stand disposed in the canister below the pull top, the stand having a platform disposed below the pull top with a plurality of platform openings therein, the stand having a plurality of legs, inside the canister, at the perimeter side wall of the canister and supporting the platform above a bottom wall of the canister.

13. A device in accordance with claim 12, wherein the grid further comprises:
   a dial pivotally disposed on the stand and below the pull top, and having a plurality of dial openings selectively alignable with the plurality of platform openings of the stand.

14. A device in accordance with claim 12, further comprising:
   a pair of stops formed on the bottom wall of the canister and on opposite sides of a leg of the plurality of legs to resist pivoting of the stand along with the dial.

15. A device in accordance with claim 12, wherein the pull top includes a lid with a perimeter secured to the canister and an aperture therein releasably closed by the pull top; and wherein the aperture is smaller than the grid so that the perimeter of the lid extends over the canister and the grid to maintaining the grid or louver in canister.

16. A device in accordance with claim 12, wherein pull top includes a lid with an annular outer portion with an outer perimeter fixed to the canister and an inner perimeter defining the aperture; wherein the pull top includes an inner portion spanning the aperture of the outer portion and having an outer perimeter releasably secured to the inner perimeter of the outer portion.

17. A device in accordance with claim 12, wherein the grid further comprises:
   a) the stand having a center axel hole and a plurality of perimeter slots;
   b) a dial pivotally disposed on the stand and below the pull top, the dial having a central axel received in the axel hole of the stand, the dial having a plurality of perimeter fingers each received in a different one of the plurality of perimeter slots of the stand, the dial having a plurality of dial openings selectively alignable with the plurality of platform openings of the stand; and
   c) the dial and the stand with the respective plurality of dial openings and the plurality of stand openings defining a scent control top disposed over the fragrant material and below the pull top, and thus contained inside the container when the pull top is secured to the canister, and exposed when the pull top is separated from the canister.

18. A device in accordance with claim 17, wherein each of the plurality of fingers has an enlarged distal end press-fit through a different one of the plurality of perimeter slots of the stand.

* * * * *